United States Patent
Pontell

(10) Patent No.: US 10,856,925 B1
(45) Date of Patent: Dec. 8, 2020

(54) SYSTEM AND METHOD FOR SURGICAL CORRECTION OF BUNION

(71) Applicant: David Pontell, McLean, VA (US)

(72) Inventor: David Pontell, McLean, VA (US)

( * ) Notice: Subject to any disclaimer, the term of this patent is extended or adjusted under 35 U.S.C. 154(b) by 0 days.

(21) Appl. No.: 16/844,646

(22) Filed: Apr. 9, 2020

Related U.S. Application Data

(60) Provisional application No. 62/924,162, filed on Oct. 21, 2019.

(51) Int. Cl.

| | | |
|---|---|---|
| *A61B 17/90* | (2006.01) | |
| *A61B 17/88* | (2006.01) | |
| *A61B 17/72* | (2006.01) | |
| *A61B 90/00* | (2016.01) | |
| *A61B 17/84* | (2006.01) | |
| *A61B 17/56* | (2006.01) | |

(52) U.S. Cl.
CPC ...... *A61B 17/8897* (2013.01); *A61B 17/7233* (2013.01); *A61B 17/7291* (2013.01); *A61B 17/84* (2013.01); *A61B 90/36* (2016.02); *A61B 2017/565* (2013.01); *A61B 2090/376* (2016.02)

(58) Field of Classification Search
CPC . A61B 17/17; A61B 17/1703; A61B 17/1717; A61B 17/1775; A61B 17/7291; A61B 17/8897; A61B 2017/565; A61B 2090/376
USPC ............................................. 606/96, 97, 104
See application file for complete search history.

(56) References Cited

U.S. PATENT DOCUMENTS

| | | | | |
|---|---|---|---|---|
| 4,520,798 A | * | 6/1985 | Lewis | A61H 39/04 601/134 |
| 2007/0299448 A1 | * | 12/2007 | Chin | A61B 17/7059 606/276 |
| 2009/0228013 A1 | * | 9/2009 | Bourque | A61B 17/1675 606/80 |
| 2010/0324556 A1 | * | 12/2010 | Tyber | A61B 17/8625 606/62 |

(Continued)

OTHER PUBLICATIONS

"MICA(TM) Minimally Invasive Foot Surgery", Wright Medical Group (2017), 16 pages.

(Continued)

*Primary Examiner* — Eduardo C Robert
*Assistant Examiner* — David C Comstock
(74) *Attorney, Agent, or Firm* — Nath, Goldberg & Meyer; Richard C. Litman

(57) ABSTRACT

The system for surgical correction of a bunion includes a capital fragment positioner and a guide wire targeting assembly. The positioner has an L-shaped handle having a transverse post extending across the end of the long arm of the handle and two tubes at opposite ends of the post extending orthogonally to the plane of the handle. The handle extends obliquely from the post to enable fluoroscopic visualization of the capital fragment. The guide wire targeting assembly includes a lower block that may be secured to the foot by K-wires and an upper block rotatably mounted on the lower block. The upper block supports guide wire tubes and is rotated to position the guide wires across the osteotomy cut in the metatarsal bone. Cannulated fixation screws are inserted over the guide wires in proper position to fix bones on opposite sides of the osteotomy.

17 Claims, 8 Drawing Sheets

(56) References Cited

U.S. PATENT DOCUMENTS

| | | | |
|---|---|---|---|
| 2013/0030446 A1* | 1/2013 | Wayne | A61B 17/1717 |
| | | | 606/104 |
| 2013/0211462 A1* | 8/2013 | Walker | A61B 17/8875 |
| | | | 606/289 |
| 2014/0330316 A1* | 11/2014 | Kalfas | A61B 17/7049 |
| | | | 606/278 |
| 2016/0030065 A1* | 2/2016 | Claes | A61B 17/1728 |
| | | | 606/96 |
| 2016/0235414 A1* | 8/2016 | Hatch | A61B 17/151 |
| 2018/0256210 A1* | 9/2018 | Mullaney | A61B 17/6458 |
| 2020/0000464 A1* | 1/2020 | Gaston | A61B 17/17 |
| 2020/0015865 A1* | 1/2020 | Lamm | A61B 17/7291 |
| 2020/0138491 A1* | 5/2020 | Brigido | A61B 17/1728 |

OTHER PUBLICATIONS

Meyr et al., "A pictorial review of reconstructive foot and ankle surgery: hallux abductovalgus", Radiology Case (2015), vol. 9, No. 6, pp. 39-43.

* cited by examiner

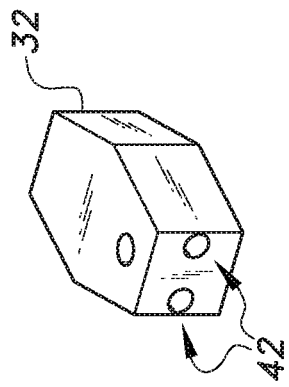
FIG. 4C
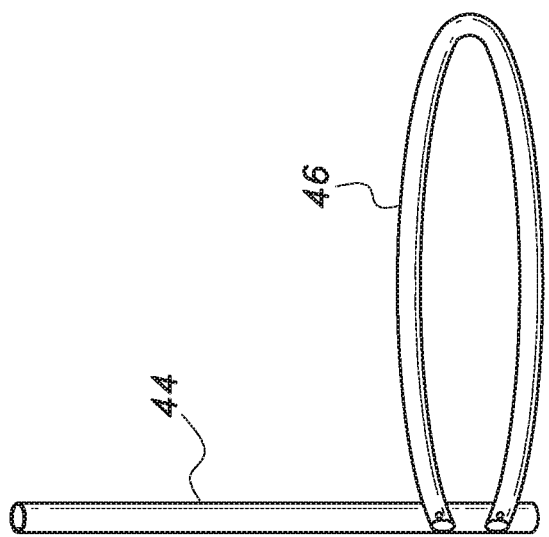
FIG. 4E
FIG. 4B
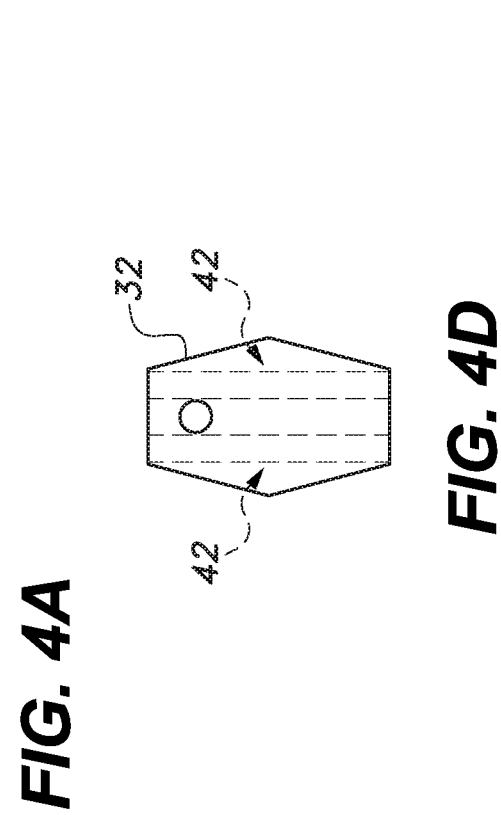
FIG. 4D
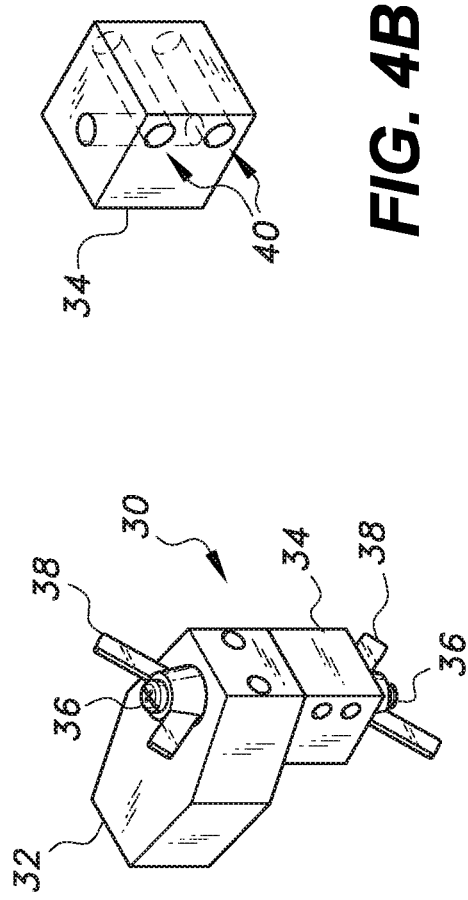
FIG. 4A

SYSTEM AND METHOD FOR SURGICAL CORRECTION OF BUNION

CROSS-REFERENCE TO RELATED APPLICATION

This application claims the benefit of U.S. Provisional Patent Application Ser. No. 62/924,162, filed Oct. 21, 2019.

BACKGROUND

1. Field

The disclosure of the present patent application relates to foot surgery, and particularly to a system and method for surgical correction of a bunion.

2. Description of the Related Art

A bunion (hallux abductovalgus) is a bump on the foot that occurs at the joint between the big toe and the head of the first metatarsal bone. As the bunion progresses, the first metatarsal bone starts to angle away from the other bones of the foot, and the big toe starts to angle inward towards the smaller toes. The condition is frequently accompanied by pain, and may affect the patient's ability to walk or engage in other weight-bearing activities. Clinically, the severity of the deformity may be evaluated by measuring the angle between various bones in the foot, including the first inter-metatarsal angle (between a longitudinal bisection of the first metatarsal bone and a longitudinal bisection of the second metatarsal), the hallux abductus angle (between the longitudinal bisection of the first metatarsal and a longitudinal bisection of the proximal phalanx of the hallux), and the metatarsal-sesamoid position (between the longitudinal bisection of the first metatarsal and the position of the tibial sesamoid). When the pain and discomfort become severe enough and the patient opts for surgical correction of the bunion, there is a variety of approaches available to the surgeon.

Bunionectomy with first metatarsal osteotomy is a common orthopedic procedure. Traditional methods employ relatively large incisions and extensive, intracapsular, soft tissue dissection (within the first MTP [metatarsophalangeal] joint) to facilitate the required reduction of angular deformity between the first and second metatarsals. Newer, minimal-incision approaches allow for equivalent angulation reduction, but without extensive soft tissue dissection (they are, largely, "extracapsular"). These minimally invasive approaches may also result in less postoperative swelling and stiffness and better cosmesis. However, this minimal-incision, "extracapsular" approach introduces technical challenges not present with conventional, open surgery, those being introduction of two, percutaneous guide wires at acute angles (~15-25° relative to the medial shaft first metatarsal), and accurate, closed-reduction of the capital fragment (the distal portion remaining after osteotomy just proximal to the head) of the first metatarsal.

The most common approach for the introduction of percutaneous guide wires to stabilize the capital fragment requires introduction of two, parallel guide wires over which cannulated bone screws are secured. The acute angle relative to the first metatarsal can make completing this task difficult, requiring multiple, sometimes, numerous attempts in order to avoid "skidding" off the medial cortex and to avoid inaccurate placement and malpositioning of the capital fragment of the first metatarsal. In addition, even if the angle of incidence is acceptable, the multiple attempts may have dulled the trocar tip of the guide wire such that it tends to deflect off the medial wall of the lateral cortex and bending without advancing, across the lateral cortex. In practice, not only is the angle acute, but the actual usable "window" through which this wire passes through the lateral cortex (which defines an acceptable position) is usually within 1 cm of the osteotomy, making accurate placement more difficult. Conventional, tubular drill guides are commonly-available and allow infinite "adjustability" of angulation, but are completely unconstrained, which may lead to positional instability. Alternatively, targeting guides that are currently in use constrain the angulation of approach for wire introduction, but still remain relatively mobile and are not infinitely-adjustable, not necessarily allowing for easy accommodation of either very shallow or less-acute angular approaches, as dictated by individual, anatomic variations.

With respect to instability of the first metatarsal head/capital fragment, the extracapsular approach with minimally invasive bunionectomy produces excellent mobility of the capital fragment to reduce angular deformity, but at the expense of instability in the sagittal, coronal, and transverse planes. This capital fragment instability is undesirable, as this may predispose to malposition (especially, plantarflexion or dorsiflexion) and postoperative complications. Current methods to avoid malpositioning employ manual reduction and reliance on accurate "preplacement" of at least one percutaneous guide wire (with the associated problems noted above), which is advanced across the oseotomy for provisional stabilization. While existing devices aid in repositioning, no device specifically-designed to accurately-position the capital fragment in the three cardinal body planes exists.

Thus, a system and method for surgical correction of a bunion solving the aforementioned problems is desired.

SUMMARY

The system for surgical correction of a bunion includes a capital fragment positioner and a guide wire targeting assembly. The positioner has an L-shaped handle having a transverse post extending across the end of the long arm of the handle and two tubes at opposite ends of the post extending orthogonally to the plane of the handle. The short arm of the handle extends obliquely from the handle to enable fluoroscopic imaging of the capital fragment. The guide wire targeting assembly includes a lower block that may be secured to the foot by K-wires and an upper block rotatably mounted on the lower block. The upper block supports guide wire tubes and is rotated to position the guide wires across the osteotomy cut in the metatarsal bone. Cannulated fixation screws are inserted over the guidewires in proper position to fix bones on opposite sides of the osteotomy.

The method for surgical correction of a bunion includes temporarily fixing the capital fragment positioner to the head of the first metatarsal near the metatarsophalangeal joint using K-wires; temporarily fixing the guide wire targeting assembly to the foot using K-wires extending through the lower block and secured in the medial cuneiform; partially extending cannulated screw guide wires through the upper block of the guide wire targeting assembly into the first metatarsal just across the lateral cortex; performing an osteotomy through the first metatarsal adjacent the head, thereby forming a capital fragment; manipulating the capital fragment with the capital fragment positioner under fluoroscopic visualization to align the first metatarsal with the proximal phalanx of the hallux; extending the cannulated screw guide wires across the osteotomy into the capital fragment; removing the K-wires and the capital fragment positioner; fixing the capital fragment to the first metatarsal using cannulated screws advanced along the cannulated screw guide wires; and removing the guide wires.

These and other features of the present disclosure will become readily apparent upon further review of the following specification and drawings.

BRIEF DESCRIPTION OF THE DRAWINGS

FIG. 4A is a perspective view of a guide wire targeting assembly component of a system for surgical correction of a bunion.

FIG. 4B is a perspective view of the lower block of the guide wire targeting assembly of FIG. 4A.

FIG. 4C is a perspective view of the upper block of the guide wire targeting assembly of FIG. 4A.

FIG. 4D is a top view of the upper block of FIG. 4C.

FIG. 4E is a front view of an exemplary guide wire tube used in the guide wire targeting assembly of FIG. 4A.

Similar reference characters denote corresponding features consistently throughout the attached drawings.

DETAILED DESCRIPTION OF THE PREFERRED EMBODIMENTS

The system for surgical correction of a bunion includes a capital fragment positioner and a guide wire targeting assembly. The positioner has an L-shaped handle having a transverse post extending across the end of the long arm of the handle and two tubes at opposite ends of the post extending orthogonally to the plane of the handle. The short arm of the handle extends obliquely from the handle to enable fluoroscopic visualization of the capital fragment. The guide wire targeting assembly includes a lower block that may be secured to the foot by K-wires and an upper block rotatably mounted on the lower block. The upper block supports guide wire tubes and is rotated to position the guide wires across the osteotomy cut in the metatarsal bone. Cannulated fixation screws are inserted over the guidewires in proper position to fix bones on opposite sides of the osteotomy.

Figure 1B:
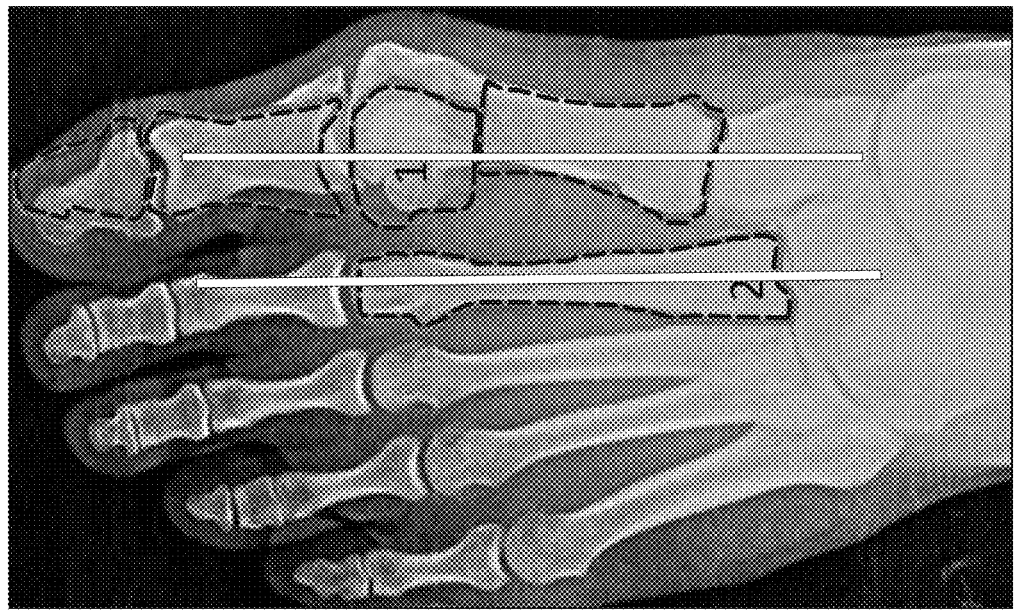
FIG. 1B is an X-ray photograph of the foot of FIG. 1A, shown after surgical correction of the bunion
Figure 1A:
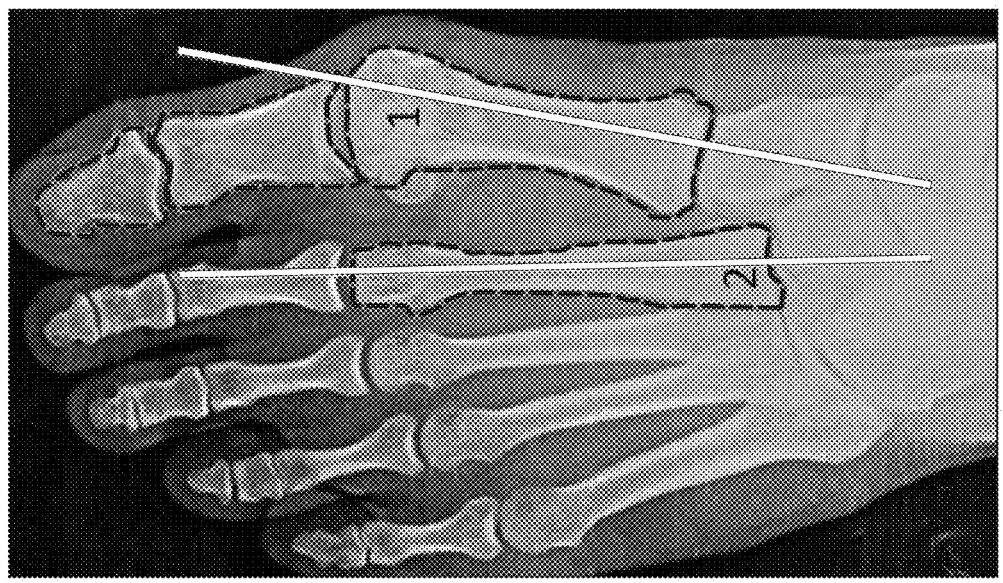
FIG. 1A is an X-ray photograph showing the left foot of a patient afflicted with a typical bunion.
Figure 2:
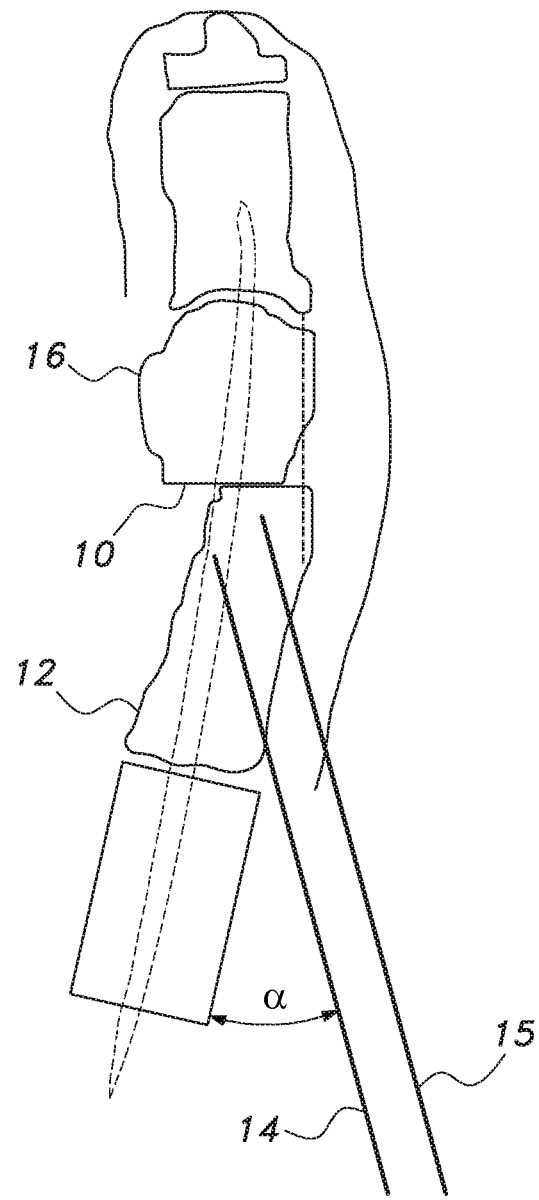
FIG. 2 is a diagrammatic top view of a foot after osteotomy of the first metatarsal for correction of a bunion, showing the desired angulation of guide wires for fixation screws relative to the first metatarsal.

FIG. 1A shows a foot afflicted by a bunion, as reflected by the large first intermetatarsal angle between the first and second metatarsals and the large hallux abductor angle between the first metatarsal and the proximal phalanx of the hallux (big toe). FIG. 1B shows the foot after surgical reduction. Although the longitudinal axis of the first metatarsal is not exactly parallel to a longitudinal axis through the second metatarsal, the angle between the two bones has been reduced so that it is within acceptable limits, and the proximal phalanx of the big toe is now substantially parallel to the adjoining toe. This result is produced by a minimally invasive surgical technique that involves an osteotomy near the head of the first metatarsal 12 accompanied by the insertion of parallel guide wires 14, 15 at an angle α between 15-25° relative to the first metatarsal 12, as shown in FIG. 2, for the insertion of cannulated fixation screws and accurate closed reduction of the capital fragment 16 of the first metatarsal 12.

Figure 3A:
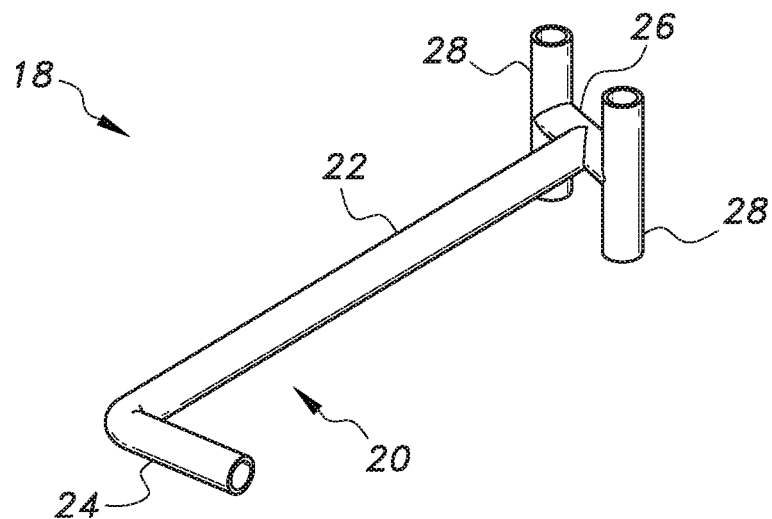
FIG. 3A is a perspective view of a capital fragment positioner component of a system for surgical correction of a bunion.
Figure 3B:
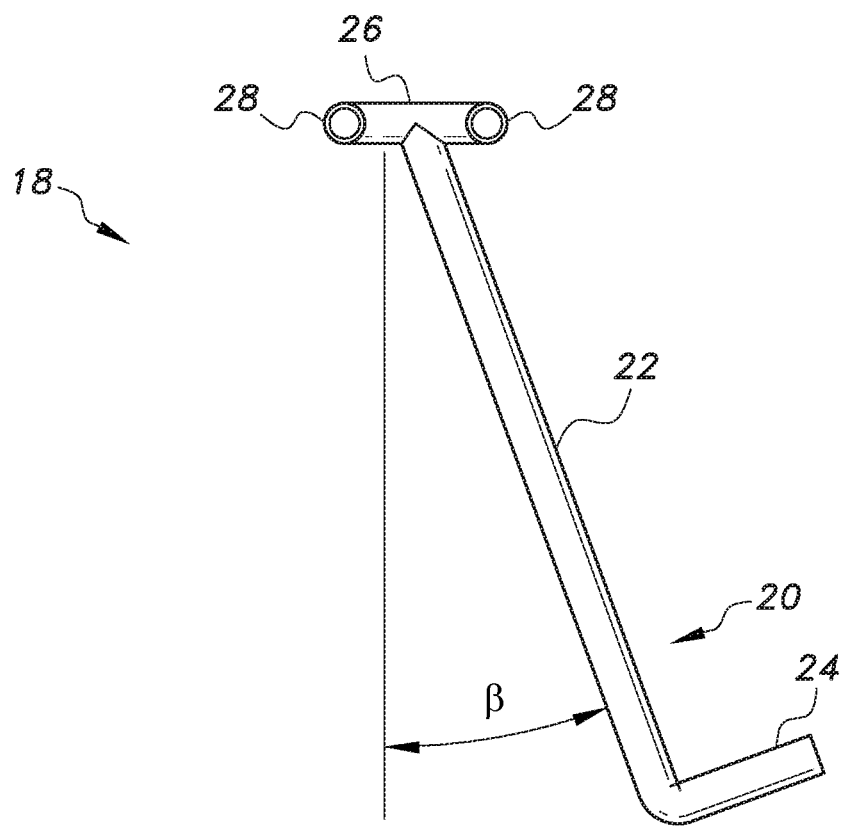
FIG. 3B is a top view of the capital fragment positioner of FIG. 3A.

The system and method involve the use of a capital fragment positioner 18, shown in FIGS. 3A and 3B. The positioner 18 includes a substantially L-shaped handle 20 having a long arm 22 and a short arm 24 extending orthogonally from the handle 20. A short post 26 is mounted transversely across the end of the long arm 22 opposite the short arm. A pair of small tubes 28 are mounted at opposite ends of the post 26 and extend orthogonal to a plane defined by the handle 20. The tubes 28 are dimensioned and configured to allow passage of 0.045" diameter K-wires through the tubes 28 immediately on either side of the extensor hallucis longus tendon just proximal to the first metatarsophalangeal joint for temporarily fixing the positioner 18 to the first metatarsal 12. The long arm 22 of the handle 20 is sloped at an angle β of about 20° relative to an axis normal to the post 26. The angulation of the arms 22, 24 of the handle 20 s designed to permit clear fluoroscopic imaging of the capital fragment 16 and the osteotomy during use for accurate positioning of the capital fragment 16. The handle 20 and the post 26 may be made from solid or tubular stainless steel stock.

The system and method also involve the use of a guide wire targeting assembly 30, shown in FIGS. 4A-4E. As shown in FIG. 4A, the assembly 30 includes an upper block 32 rotatably mounted on a lower block 34. In the exemplary embodiment shown in the Figures, rotation is enabled by a bolt 36 extending through the upper block 32 and the lower block 34 that can be secured by wingnuts 38 or other releasable fasteners to temporarily fix the upper block 32 at an infinitely adjustable angle with respect to the lower block 34. However, it will be obvious to those of ordinary skill in the art that hardware other than a bolt 36 and wingnuts 38 may be provided that will allow the upper block 32 to rotate 360° on top of the lower block and be temporarily fixed when a desired angular orientation is obtained. As shown in FIG. 4B, the lower block 34 may be a rectangular prism having a pair of throughbores 40 defined therein extending from one face to the opposite face. Exemplary dimensions for the lower block 34 may be, e.g., 1 cm by 1 cm by 0.7 cm. The throughbores 40 have a diameter sufficient to allow the passage of 0.062" K-wires to secure the lower block to the medial cuneiform, e.g., 2 mm diameter, and may be aligned and spaced apart vertically by 1 mm spacing.

As shown in FIGS. 4C and 4D, the upper block 32 is symmetrical, and may also be a rectangular prism, but with the front and rear corners beveled. The upper block 32 has a pair of parallel, horizontally aligned throughbores 42 defined therein extending from the front face to the rear face. The throughbores 42 may be spaced on opposite sides of the bolt 36, and have a diameter of about 4 mm, or at least sufficient for temporary mounting of guide wire tubes 44 having a diameter of about 3 mm for passage of guide wires through the upper block 32. Exemplary dimensions of the upper block may be 2.5 cm by 2.0 cm by 0.7 cm. An exemplary guide wire tube 44 is shown in FIG. 4E. The guide wire tubes 44 may optionally include a bent handle 46 for ease in handling.

Figure 5:
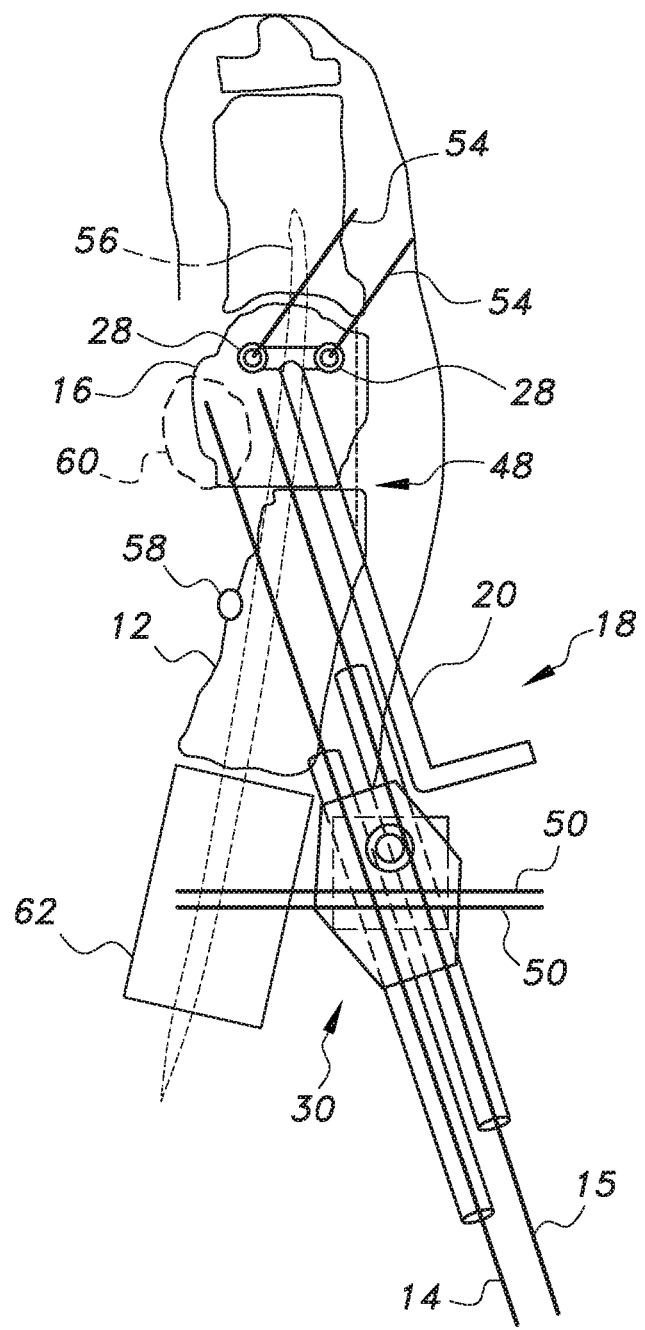
FIG. 5 is a diagrammatic top view of the first metatarsal and phalanx of a foot after an osteotomy to correct a bunion, showing positioning of the capital fragment positioner and guide wire targeting assembly.

Referring to FIG. 5, in use, two 0.045" K-wires 54 are inserted through the tubes 28 of the capital fragment positioner 18 into the head of the first metatarsal 12 proximal to the first metatarsophalangeal joint on opposite sides of the extensor hallucis longus tendon 56. The positioner 18 is left in place while the first metatarsal osteotomy 48 is cut, then the small L-handle 20 is moved like a "joystick," angulating the capital fragment 16 such that intraoperative fluoroscopy images confirm good reduction in the transverse, coronal, and sagittal planes. Once this position is confirmed, the guide wires 14, 15 can then be advanced across the osteotomy 48, securing this provisional fixation, and once rechecked as to position, the cannulated screws are advanced and secured for permanent fixation. These temporary guide wires 14, 15 and the K-wires 54 in the positioner 18 are then removed.

The guide wire targeting assembly 30 is held against the skin of the medial aspect of the foot and AP fluoroscopic image is obtained to confirm the tubular wire guide position will allow introduction of the first guide wire 14 at the proximal-medial corner of the first metatarsal 12, aimed to exit the lateral first metatarsal cortex between the lateral cortex midpoint 58 and the fibular sesamoid 60.

Figure 6A:
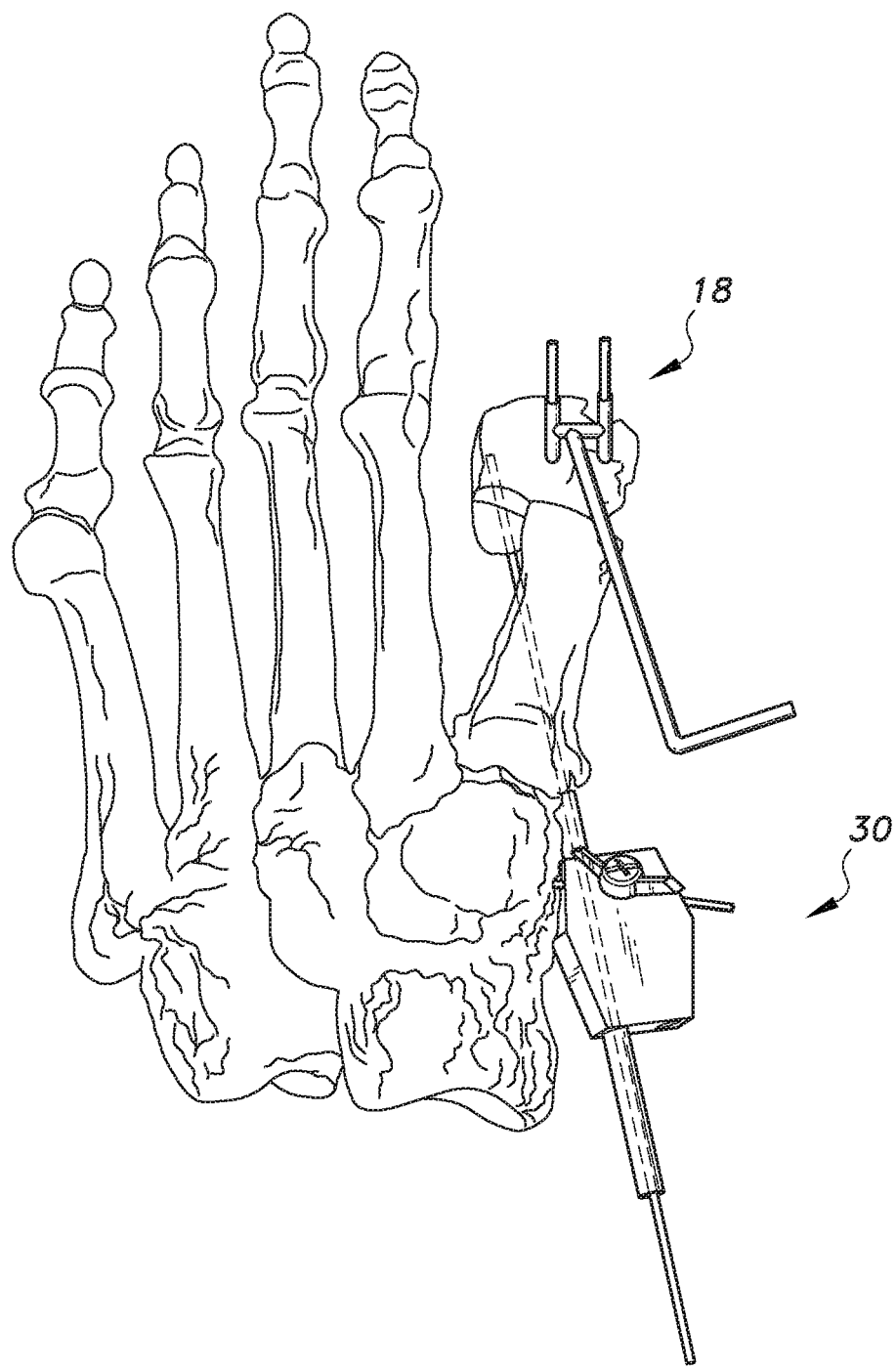
FIG. 6A is a top view of a foot, showing positioning of prototypes of the system for surgical correction of a bunion.
Figure 6B:
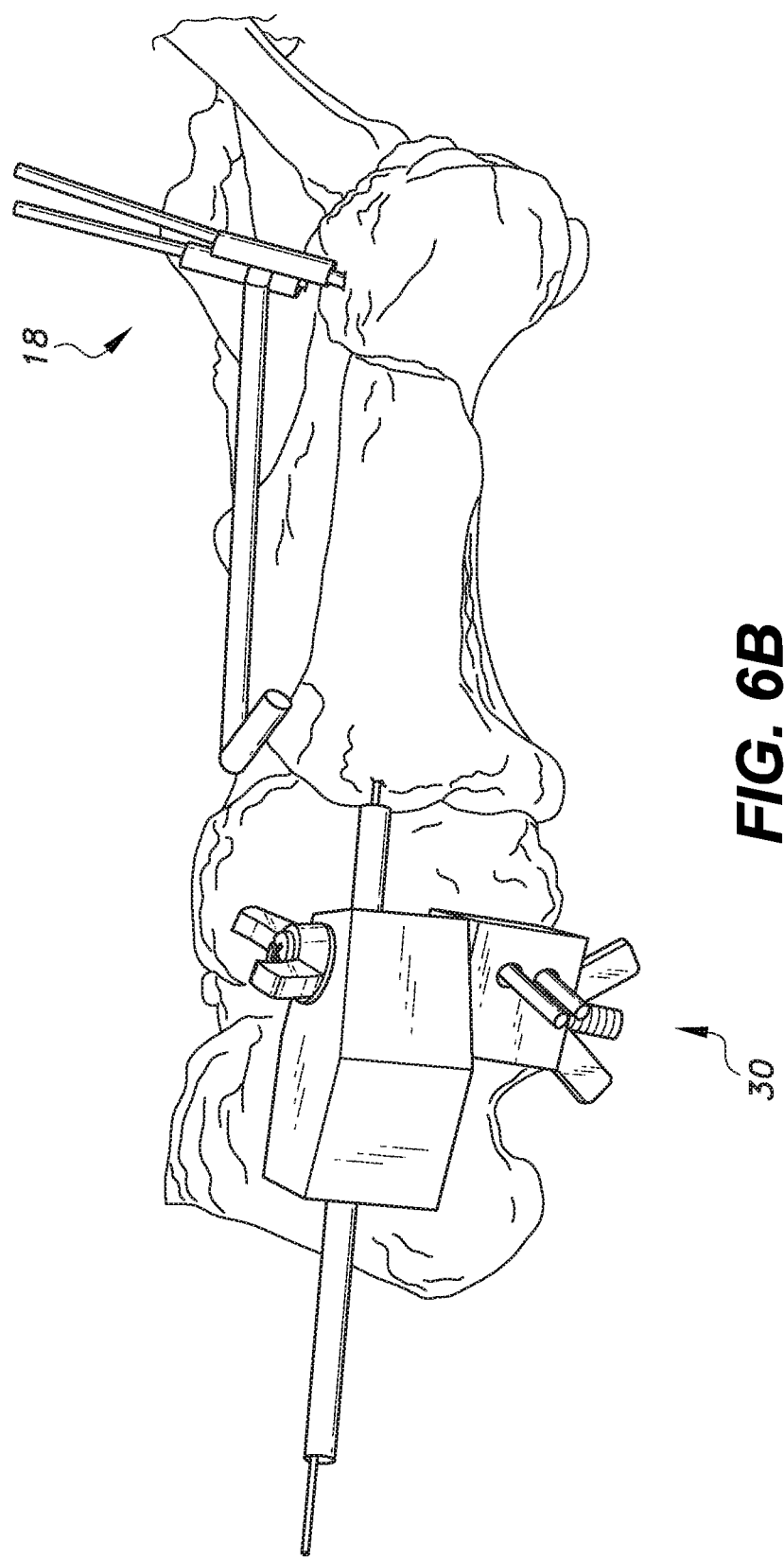
FIG. 6B is a side view of the foot of FIG. 6A, showing positioning of prototypes of the system for surgical correction of a bunion.
Figure 7:
FIG. 7 is a top view X-ray photograph of a foot after surgical correction of a bunion, showing the positioning of fixation screws after removal of the guide wires and K-wires.

This introduction point is checked on a lateral view, as well, to confirm sagittal position. Once confirmed, a 0.062" K-wire 50 is advanced transversely through one of the two lower block holes approximately perpendicular to the foot into the medial cuneiform 62 for temporary stabilization of the targeting guide assembly 30 adjacent to the medial cuneiform 62. A guide wire 14, manually-inserted into the small, tubular wire guide in the lateral targeting guide hole, allows confirmation of good positioning with AP and lateral fluoroscopic views. Once accomplished, the second temporary, transverse, K-wire 50 is inserted into the second lower block hole, locking the sagittal and frontal plane positions of the targeting guide assembly 30. Once this position is confirmed, the more medial guide-wire 15 can be advanced and the capital fragment positioner 18 utilized to insure proper head orientation. If the angle of approach of the first guide wire 14 is not optimal in the transverse plane, then the mobile, upper block position is adjusted by rotation of upper on lower block, and when optimal, secured with the wingnut, which links the upper and lower blocks. FIGS. 6A and 6B show the relative positions of the capital fragment positioner 18 and the guide wire targeting assembly 30 during the procedure. FIG. 7 shows the foot after implantation of the cannulated fixation screws 64 across the osteotomy and removal of the guide wires and K-wires.

The steps in a method of using the system for surgical correction of a bunion may be summarized as including the following: laying the capital fragment positioner on skin of a patient's foot with the tubes of the positioner on either side of the patient's extensor hallucis longus tendon; inserting K-wires through the positioner tubes to temporarily fix the positioner to the distal first metatarsal head; positioning the guide wire targeting assembly on skin of the patient's foot medial to the medial cuneiform bone using an AP fluoroscopic image; inserting a first K-wire through one of the bores of the lower block perpendicular to and into the medial cuneiform bone; inserting one of the guide tubes into a lateral one of the guide tube bores by hand to estimate direction and path of guide wire insertion; inserting a second K-wire into the other bore of the lower block and inserting the second K-wire into the medial cuneiform bone to "fix" position of lower block against the patient's foot; advancing a first (proximal) guide wire through the guide tube in the lateral guide tube bore into the medial proximal first metatarsal bone and continuing to advance until just across the lateral cortex; cutting an osteotomy in the distal first metatarsal; manipulating the capital fragment positioner to accurately position the capital fragment in transverse, sagittal, and frontal planes; advancing the first guide wire across the osteotomy so that a tip of the first guide wire ends in a lateral portion of the capital fragment; inserting a second one of the guide tubes through a medial guide tube bore in the upper block; advancing a second guide wire into the first metatarsal bone and across the osteotomy; removing the capital fragment positioner and the K-wires; inserting cannulated screws over the guide wires and through the osteotomy into the bones; removing the guide wires; and completing skin closure.

It is to be understood that the system and method for surgical correction of a bunion is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A system for surgical correction of a bunion, comprising:
   a capital fragment positioner having:
   an L-shaped handle having an elongated long arm and a short arm, the long arm having a proximal end and a distal end, the short arm extending from the proximal end orthogonal to the long arm, the long arm and the short arm defining a plane of the handle;
   a transverse post extending across the distal end of the long arm, the transverse post having opposing ends, the transverse post and the long arm defining an obtuse angle; and
   first and second tubes extending from the opposing ends of the transverse post, respectively, each of the first and second tubes extending orthogonal to the plane of the handle; and
   a guide wire targeting assembly having:
   a lower block, the lower block having a top surface, opposing side surfaces, opposing end surfaces, and a bottom surface, the lower block having a pair of bores extending between the opposing side surfaces, the bores being dimensioned and configured for insertion of K-wires therethrough for temporarily fixing the lower block to a medial cuneiform bone of a foot;
   a pivot pin extending from the top surface of the lower block;
   an upper block rotatably mounted on the pivot pin, the upper block having a pair of guide tube bores extending transversely therethrough;
   a pair of guide tubes removably extending through the guide tube bores; and
   at least one releasable fastener attached to the pivot pin, the releasable fastener being adapted for releasably locking the upper block to the lower block to temporarily fix the guide tubes in a selected orientation.

2. The system for surgical correction of a bunion according to claim 1, wherein the handle arms and the post of said capital fragment positioner are made from solid stainless steel stock.

3. The system for surgical correction of a bunion according to claim 1, wherein the handle arms and the post of said capital fragment positioner are made from tubular stainless steel stock.

4. The system for surgical correction of a bunion according to claim 1, wherein the long arm of said handle is sloped at an angle of about 20 relative to an axis normal to the post.

5. The system for surgical correction of a bunion according to claim 1, wherein the upper block of said guide wire targeting assembly is symmetrical.

6. The system for surgical correction of a bunion according to claim 5, wherein the upper block of said guide wire targeting assembly is rotatable 360° around the pivot pin.

7. The system for surgical correction of a bunion according to claim 5, wherein the pivot pin of said guide wire targeting assembly comprises a bolt and the at least one releasable fastener comprises a wingnut.

8. A method of using the system of claim 1 for surgical correction of a bunion, comprising the steps of:
 laying the capital fragment positioner on skin of a patient's foot with the tubes of the positioner on either side of the patient's extensor hallucis longus tendon;
 inserting K-wires through the positioner tubes to temporarily fix the positioner to the distal first metatarsal head;
 positioning the guide wire targeting assembly on skin of the patient's foot medial to the medial cuneiform bone using an AP fluoroscopic image;
 inserting a first K-wire through one of the guide wire bores of the lower block perpendicular to and into the medial cuneiform bone;
 inserting one of the guide tubes into a lateral one of the guide tube bores by hand to estimate direction and path of guide wire insertion;
 inserting a second K-wire into the other guide wire bore of the lower block and inserting the second K-wire into the medial cuneiform bone to "fix" position of the lower block against the patient's foot;
 advancing a first (proximal) guide wire through the guide tube in the lateral guide tube bore into the medial proximal first metatarsal bone and continuing to advance the first guide wire until just across the lateral cortex;
 cutting an osteotomy in the distal first metatarsal;
 manipulating the capital fragment positioner to accurately position the capital fragment in transverse, sagittal, and frontal planes;
 advancing the first guide wire across the osteotomy so that a tip of the first guide wire ends in a lateral portion of the capital fragment;
 inserting a second one of the guide tubes through a medial guide tube bore in the upper block;
 advancing a second guide wire into the first metatarsal bone and across the osteotomy;
 removing the capital fragment positioner and the K-wires;
 inserting cannulated screws over the guide wires and through the osteotomy into the bones;
 removing the guide wires; and
 completing skin closure.

9. The method of claim 8, further comprising the step of confirming positioning of the guide wires and positioning of the capital fragment by fluoroscopic imaging.

10. The method of claim 8, further comprising the steps of:
 temporarily removing the capital fragment positioner prior to said step of cutting the osteotomy; and
 reattaching the capital fragment positioner prior to said step of manipulating the capital fragment positioner.

11. A kit for surgical correction of a bunion, comprising:
 the capital fragment positioner of claim 1; and
 the guide wire targeting assembly of claim 1.

12. A capital fragment positioner for positioning a bone fragment for fixation following an osteotomy, comprising:
 an L-shaped handle having an elongated long arm and a short arm, the long arm having a proximal end and a distal end, the short arm extending from the proximal end orthogonal to the long arm, the long arm and the short arm defining a plane of the handle;
 a transverse post extending across the distal end of the long arm, the transverse post having opposing ends, the transverse post and the long arm defining an obtuse angle; and
 first and second tubes extending from the opposing ends of the transverse post, respectively, each of the first and second tubes extending orthogonal to the plane of the handle,
 wherein the long arm of the handle is sloped at an angle of about 20° relative to an axis normal to the post.

13. The capital fragment positioner according to claim 12, wherein the handle arms and the post of said capital fragment positioner are made from solid stainless steel stock.

14. The system for surgical correction of a bunion according to claim 12, wherein the handle arms and the post of said capital fragment positioner are made from tubular stainless steel stock.

15. A guide wire targeting assembly for installing guide wires to align a bone fragment with a bone following an osteotomy, comprising:
 a lower block, the lower block having a top surface, opposing side surfaces, opposing end surfaces, and a bottom surface, the lower block having a pair of bores extending between the opposing side surfaces, the bores being dimensioned and configured for insertion of K-wires therethrough for temporarily fixing the lower block to a bone;
 a pivot pin extending from the top surface of the lower block;
 an upper block rotatably mounted on the pivot pin, the upper block having a pair of guide tube bores extending transversely therethrough, wherein the upper block of the guide wire targeting assembly is rotatable 360° around the pivot pin;
 a pair of guide tubes removably extending through the guide tube bores; and
 at least one releasable fastener attached to the pivot pin, the releasable fastener being adapted for releasably locking the upper block to the lower block to temporarily fix the guide tubes in a selected orientation.

16. The guide wire targeting assembly according to claim 15, wherein the upper block of said guide wire targeting assembly is symmetrical.

17. The guide wire targeting assembly according to claim 15, wherein the pivot pin of said guide wire targeting assembly comprises a bolt and the at least one releasable fastener comprises a wingnut.

* * * * *